(12) United States Patent
Pohl et al.

(10) Patent No.: US 9,905,990 B1
(45) Date of Patent: Feb. 27, 2018

(54) BACKGROUND REMOVAL FROM RAMAN SPECTRA BY AN INTRACAVITY ACTIVE-TUNING ELEMENT FOR A LASER

(71) Applicant: Alakai Defense Systems, Inc., Largo, FL (US)

(72) Inventors: Ken Pohl, Largo, FL (US); Matthew King, Largo, FL (US); Adam J. Hopkins, Largo, FL (US); Alan Ford, Largo, FL (US)

(73) Assignee: Alakai Defense Systems, Inc., Largo, FL (US)

( * ) Notice: Subject to any disclaimer, the term of this patent is extended or adjusted under 35 U.S.C. 154(b) by 133 days.

(21) Appl. No.: 14/689,964

(22) Filed: Apr. 17, 2015

Related U.S. Application Data (60) Provisional application No. 61/980,902, filed on Apr. 17, 2014.

(51) Int. Cl.
*H01S 3/106* (2006.01)
*G01N 21/65* (2006.01)
(Continued)

(52) U.S. Cl.
CPC .......... *H01S 3/1062* (2013.01); *G01N 21/65* (2013.01); *H01S 3/0809* (2013.01); *H01S 3/107* (2013.01); *H01S 3/1055* (2013.01); *H01S 3/1068* (2013.01)

(58) Field of Classification Search
CPC .......... G01N 21/65; G01J 3/44; H01S 3/1062; H01S 3/0809; H01S 3/1055; H01S 3/1068; H01S 3/107; H01S 5/141
See application file for complete search history.

(56) References Cited

U.S. PATENT DOCUMENTS 3,548,337 A 12/1970 Gates et al.
3,769,608 A 10/1973 Vargady
(Continued)

FOREIGN PATENT DOCUMENTS

EP 1054490 A2 7/2004

OTHER PUBLICATIONS

Andrew P. Shreve, Nerine J. Cherepy, and Richard A. Mathies, "Effective Rejection of Fluorescence Interference in Raman Spectroscopy Using a Shifted Excitation Difference Technique," Applied Spectroscopy, vol. 46, No. 4, 1992.*
(Continued)

*Primary Examiner* — Kara E Geisel
*Assistant Examiner* — Violeta A Prieto
(74) *Attorney, Agent, or Firm* — McKee, Voorhees & Sease, PLC (57) ABSTRACT

A system, apparatus, and method for multiple wavelength Raman interrogation laser generation and Raman spectra acquisition. An intracavity laser tuning subsystem is integrated into the laser cavity. The tuning subsystem allows switching between at least two laser output frequencies in a manner effective for good identification and separation of Raman spectra from non-Raman spectra, including autofluorescence from the sample and background. The tuning subsystem can be implemented in different ways in the cavity. It does not require material alteration of the line-narrowing components. Also, processing of acquired raw signal from the multiple wavelength interrogation can further assist effective Raman spectra identification and separation.

7 Claims, 9 Drawing Sheets

(51) Int. Cl.
*H01S 3/08* (2006.01)
*H01S 3/1055* (2006.01)
*H01S 3/107* (2006.01)

(56) References Cited

U.S. PATENT DOCUMENTS

| | | | |
|---|---|---|---|
| 3,775,699 A | 11/1973 | Cassels | |
| 4,081,760 A | 3/1978 | Berg | |
| 5,331,651 A | 7/1994 | Becker et al. | |
| 5,432,610 A * | 7/1995 | King | G01N 21/65 |
| | | | 356/301 |
| 5,786,893 A | 7/1998 | Fink et al. | |
| 5,856,869 A | 1/1999 | Cooper et al. | |
| 6,075,252 A * | 6/2000 | Atkinson | G01N 21/39 |
| | | | 250/339.13 |
| 6,304,586 B1 * | 10/2001 | Pease | H01S 5/02248 |
| | | | 356/221 |
| 6,486,574 B2 | 11/2002 | Botos et al. | |
| 6,639,715 B2 | 10/2003 | Naito et al. | |
| 6,870,629 B1 * | 3/2005 | Vogel | G01M 11/331 |
| | | | 356/519 |
| 6,917,420 B2 | 7/2005 | Traber | |
| 6,967,976 B2 | 11/2005 | Xie et al. | |
| 7,145,651 B2 | 12/2006 | Li et al. | |
| 7,245,369 B2 | 7/2007 | Wang et al. | |
| 7,403,281 B2 | 7/2008 | Carron et al. | |
| 7,545,493 B2 | 6/2009 | Wang et al. | |
| 7,864,311 B2 | 1/2011 | Klehr et al. | |
| 8,554,344 B2 | 10/2013 | Sun et al. | |
| 8,570,507 B1 | 10/2013 | Cooper et al. | |
| 8,718,105 B2 | 5/2014 | Weida et al. | |
| 2002/0126345 A1* | 9/2002 | Green | G02B 5/281 |
| | | | 398/65 |
| 2008/0204715 A1* | 8/2008 | Klehr | G01J 3/10 |
| | | | 356/73 |
| 2010/0193710 A1* | 8/2010 | Wakabayashi | B82Y 20/00 |
| | | | 250/504 R |

OTHER PUBLICATIONS

Iacopo, Osticioli, et al., "Shift-Excitation Raman Difference Spectroscopy-Difference Deconvolution Method for the Luminescence Background Rejection From Raman Spectra of Solid Samples", Applied Spectroscopy, vol. 61, No. 8, (May 11, 2007), pp. 839-844.

De Luca, Anna Chiara, et al., "Online Fluorescence Suppression in Modulated Raman Spectroscopy", Analytical Chemistry, vol. 82, No. 2, (Jan. 15, 2010), pp. 738-745.

McCain, Scott T., et al., "Multi-Excitation Raman Spectroscopy Technique for Fluorescence Rejection", Optics Express, vol. 16, No. 15, (Jul. 21, 2008), pp. 10975-10991.

Cooper, John B., et al., "Sequentially Shifted Excitation Raman Spectroscopy: Novel Algorithm and Instrumentation for Fluorescence-Free Raman Spectroscopy in Spectral Space", Applied Spectroscopy, vol. 67, No. 8, (Apr. 3, 2013), pp. 973-984.

Martins, Mario Augusto da Silva, et al., "Shifted-Excitation Raman Difference Spectroscopy for in vitro and in vivo Biological Samples Analysis", Biomedical Optics Express, vol. 1, No. 2, (Sep. 1, 2010), pp. 617-626.

\* cited by examiner

BACKGROUND REMOVAL FROM RAMAN SPECTRA BY AN INTRACAVITY ACTIVE-TUNING ELEMENT FOR A LASER

CROSS-REFERENCE TO RELATED APPLICATIONS

This application claims the benefit of and priority under 35 U.S.C. § 119 to provisional application Ser. No. 61/980,902, filed Apr. 17, 2014, incorporated by reference herein in its entirety.

BACKGROUND OF THE INVENTION

Field of Invention

The present invention relates to chemical detection utilizing Raman spectroscopy, including but not limited to military use and, in particular, to apparatus and methods for efficiently interrogating a sample (e.g. solids, liquids, solutions, mixtures) at different laser wavelengths to allow acquisition of multiple Raman spectra from the sample to assist in separating Raman information about the sample from background signal, including fluorescence excited by the laser.

Related Art

The value of Raman spectroscopy for an ever-increasing variety of applications is widely discussed in the literature. One example is non-destructive detection of one or more chemical constituents of potentially dangerous or harmful objects or substances, such as explosives, chemical warfare agents, and toxic industrial chemicals. Non-destructive interrogation of such things, at a reasonable stand-off distance, can be invaluable. Raman spectroscopy has applications in other areas, including but not limited to, pharmaceutical, petrochemical, and other manufacturing/inspection processes.

As will be discussed further below, Raman spectroscopy has a technical hurdle for many of its proposed applications. Raman scattering from an interrogation energy (e.g. laser beam) normally consists of a minute (e.g. on the order of $1:10^9$) fraction of the total scattering. Non-Raman signal dominates. Many times auto-fluorescence from the target caused by the interrogating laser is returned and obscures or confounds the Raman spectra. A variety of attempts to overcome this hurdle have been proposed in the literature. This includes interrogating the target at more than one laser wavelength. Comparison of the returned total signal at different laser interrogation wavelengths has been found to help identify and separate Raman spectra from non-Raman spectra. Non-Raman spectra can include Rayleigh scattering, auto-fluorescence, and background noise, However, the inventors have identified that there is room for improvement in the manner in which different interrogation laser wavelengths can be created. They have also identified beneficial techniques for controlling spectra acquisition from the multiple wavelength interrogations. As can be appreciated by' those skilled in this technical field, a variety of factors can be relevant to the design and operation of a Raman spectrometer, Several have been discussed above. But additional factors can complicate such design. Some laser sources are tunable but not over a large bandwidth, This limits its performance regarding Raman spectroscopy. It is possible to add somewhat complex components including multiple lasers to get different laser wavelengths, as exemplified in US Pat. No. 7,245,369, incorporated by reference herein, but this can be expensive and impractical. Therefore, the factors regarding how a laser source can be tuned over effective and efficient bandwidth by relatively noncomplex techniques are not necessarily straightforward because of competing and sometimes antagonistic factors involved. Economy also can come into play. Many of the systems proposed in the state of the art do not meet these tests. Some require separate components, such as a laser cavity and some sort of device outside the cavity to control switching or change of laser wavelengths. Others utilize relatively expensive components. Still others need laboratory-type controlled settings. And, further, some systems require very accurate calibration or settings to work adequately. This would seem to make sense because of the small amount of detectible energy involved and the issues of signal to noise discussed earlier.

In particular, for non-laser diode laser generation, a laser gain medium in a laser cavity is needed. Line narrowing components or elements are included to produce a line-narrowed laser for effective laser interrogation of a target or sample for acquiring Raman spectra. However, satisfactory techniques for tuning a laser over a satisfactory gain bandwidth have not been identified in the art.

Therefore, the inventors have identified a need in the art for improvement regarding apparatus and methods for acquiring Raman spectra at different interrogation laser wavelengths, including use with Raman spectroscopy for chemical detection.

SUMMARY OF THE INVENTION

Therefore, it is a principle object, feature, aspect, or advantage of the invention to present systems, apparatus, and methods for multiple wavelength Raman spectra acquisition which improves over or solves problems and deficiencies in the art.

The present invention relates to systems, apparatus, and methods to generate plural laser wavelengths from a single non-diode (e.g. gas and solid state) laser source by a laser intracavity tuning element or subsystem. It avoids having to use a separate laser source, complex components or controls, resource intensive calibration, or extreme precision and accuracy in operation for effectiveness. It allows implementation in a variety of configurations, including in a single instrument. It can avoid having to alter the line-narrowing components or elements of the laser generation sub-system.

In one aspect of the invention, the laser tuning element is built into the laser cavity and allows controllable switching between at least two states with a single instrument. Each state results in generation of different laser output wavelengths which can be impinged on a target. This allows acquisition of spectral information at the different laser wavelengths. The controllable timing is over a significant gain bandwidth. A controllable modulation or tuning element adjusting path length through the gain medium provides such tuning. As a result, the signal is boosted which improves detection performance relative to Raman information. That raw spectral information can be processed to separate and use the Raman spectra.

In aspects of the invention, the modulation or tuning element can take the form of an etalon imposing in the optical path of the laser cavity on the side of the gain element opposite the output coupler. The etalon can be rotated or otherwise adjusted to different angular orientations relative the optical path to produce the different laser output wavelengths. An actuator can be instructed to rotate or adjust the etalon in a manner correlated to a laser interrogation and acquisition of raw spectral data back from the sample or target so that information about the wavelength and acquired data can be maintained. In this manner, a relatively simple, effective, compact, and economical multiple wavelength Raman spectra acquisition can be accomplished.

In other aspects of the invention, the tuning element can take different forms. One example is plural sets of a fixed cavity end mirror and etalon, but at different spatial positions relative the optical axis to the gain medium and output coupler. A switching device or actuator can select between sets for generation of different laser wavelengths. Essentially this provides intracavity alternative optical paths that can he selected for different laser wavelengths. Other alternatives are control of acousto-optic modulators, Pockels cells, or spinning reflectors to select between alternative sets of mirror/etalon combinations, each of which produces a different laser wavelength.

Further aspects of the invention include techniques to synchronize or correlate the laser interrogation with the spectral acquisition, and to process the acquired information to extract the Raman data over a significant gain bandwidth to improve detection performance.

Further objects, features, aspects, and/or advantages of the present invention will become more apparent with reference to the accompanying specification and claims.

BRIEF DESCRIPTION OF IHE DRAWINGS

The drawings accompanying this description are intended to illustrate exemplary embodiments and methodologies of aspects of the invention. A brief summary of what the drawings are intended to illustrate is as follows.

FIG. 3A are for laser wavelengths one FWHM apart, FIG. 3B for laser wavelengths two FWHM apart, and FIG. 3C for three laser wavelengths, two of which are generated simultaneously from one étalon position and the third from a different étalon position, in which the total laser energy at each étalon position is known.

DETAILED DESCRIPTION OF EXEMPLARY EMBODIMENTS OF THE INVENTION

Overview

For a better understanding of the invention, several examples of forms it can take will now be described in detail. It is to be understood, however, that these exemplary embodiments are neither inclusive nor exclusive of the invention.

In this description, frequent reference will be taken to the drawings, which are itemized above. Reference numerals will be used to indicate certain parts and locations in the drawings. The same reference numerals will be used to indicate the same or similar parts or locations throughout the drawings, unless otherwise indicated.

Further Background

Raman spectroscopy is becoming more and more common for non-contact detection and sample characterization. It has found numerous uses in a variety of fields. Continual improvements to Raman spectroscopy hardware-in particular, more compact, efficient, and powerful laser sources—make it likely to find even more applications than its current employment.

Unfortunately, Raman spectroscopy is not without its disadvantages, one of the biggest of which is a potentially high background signal. The background is often caused by fluorescence emission initiated from the same laser source that excites Raman scattering. The fluorescence is typically far more intense than Raman scattered light and can overwhelm the detector such that only the fluorescence signal is observed. Consequently, it is desirable to mitigate or avoid the fluorescence background as much as possible.

Several strategies have been proposed to deal with the fluorescence background problem. Using lasers in the near-IR region is one strategy. Near-IR radiation does not stimulate as much fluorescence as visible and ultraviolet (UV) lasers since fluorescence often increases with decreasing excitation wavelength. However, the Raman scattering signal is greatly reduced for a given laser power in the near-IR compared to sources at shorter wavelengths ($\lambda$) because of a $1/\lambda^4$ dependence in Raman scattering efficiency. Detector efficiencies are also generally better at wavelengths in the visible and ultraviolet (UV) regions of the electromagnetic spectrum. To take advantage of the better scattering and detector efficiency, strategies for removing fluorescence by collecting Raman spectra from multiple laser wavelengths have also been proposed. See, e.g., M. A. da Silva Martins, D. G. Ribeiro, E. A. Pereira Dos Santos, A. A. Martin, A. Fontes, and H. da Silva Martinho, "Shifted-excitation Raman difference spectroscopy for in vitro and in vivo biological samples analysis.," *Biomed. Opt. Express*, vol. 1, no. 2, pp. 617-626, Jan. 2010, and J. B. Cooper, M. Abdelkader, and K. L. Wise, "Sequentially shifted excitation Raman spectroscopyu: Novel algorithm and instrumentation for fluorescence-free Raman spectroscopy in spectral space.", *J. Appl. Spec.*, vol. 67, no. 8, pp. 973-984, both incorporated by reference herein.

These methods utilize the fact that fluorescence spectra depend only weakly on the laser wavelength for small changes in laser wavelength, but Raman spectra shift linearly with laser wavelength for small changes in laser wavelength. Algorithms that detect differences between the spectra collected at different wavelengths can be used to separate the relatively unvarying fluorescence background from the varying Raman shift.

Examples of hardware for collecting multiple-wavelength Raman spectra for background removal purposes can be found in the literature and other patents. See, e.g., Q. Li and S. X. Wang, "Apparatus for fluorescence subtracted Raman spectroscopy," U.S. Pat. No. 7,145,651 (2006); J. Cooper, M. Abdelkader, and K. Wise, "Method and apparatus for acquiring Raman spectra without background interferences," U.S. Pat. No. 8,570,507 (2013); A. Klehr, S. Bernd, M. Maiwald, and H. Schmidt, "Method and device for producing and detecting a Raman spectrum," U.S. Pat. No. 7,864,311 (2011); S. T. McCain, R. M. Willett, and D. J. Brady, "Multi-excitation Raman spectroscopy technique for fluorescence rejection.," *Opt. Express*, vol. 16, no. 15, pp. 10975-91, July 2008; A. C. De Luca, M. Mazilu, A, Riches, C. S. Herrington, and K. Dholakia, "Online fluorescence suppression in modulated Raman spectroscopy.," *Anal. Chem.*, vol. 82, no, 2, pp. 738-45, January 2010; and I. Osticioli, A. Zoppi, and E. M. Castellucci, "Shift-Excitation Raman :Difference Spectroscopy?Difference Deconvolution Method for the Luminescence Background. Rejection from Raman Spectra of Solid Samples," *Appl. Spectrosc.*, vol. 61, no. 8, pp. 839-844, 2007; each of which is incorporated by reference herein.

Most of the hardware described to date has been focused on diode laser systems, typically at 785 nm or longer in wavelength. In these cases, the multiple-wavelength spectra are generated by using multiple diode laser sources (see, e.g. U.S. Pat. Nos. 7,545,493 and 7,245,369, incorporated by reference herein) or by modulating the wavelength of one or more diode lasers by altering the current (see, e,g. U.S. Pat. No. 7,864,311) and/or temperature (see, e.g. U.S. Pat. No. 5,856,869 incorporated by reference herein, and U.S. Pat. No. 8,570,507) of the laser and/or a corresponding wavelength selection element. Klehr describes the further selection of wavelength via an internal tunable element, such as a grating or an étalon (see, e.g. U.S. Pat. No. 7,864,311), but within the context of a tunable laser diode only. Algorithms for isolating the fluorescence and Raman signals from multi-wavelength Raman spectra are also described in the literature, often alongside the hardware, A detailed discussion is not given here, but can be found in the incorporated by reference citations above.

Apparatus/System

As will be appreciated by considering the specific examples below, the instruments to practice aspects of the invention will be part of a larger system that includes not only the multiple wavelength generation components to interrogate samples or targets with different wavelength laser energy, but also the hardware to collect/acquire a raw return signal during the interrogation times and signal processing to identify Raman spectra in the raw signal. Such collection/acquisition/processing hardware is commercially available, generally discussed in many of the incorporated-by-reference citations set forth earlier, and will not be discussed in detail here. It includes a spectrometer, which can be dispersive or Fourier-transform, and either and array or single element detector, as appropriate. The designer can select these components according to need or desire.

Similarly, the basic laser generation components, such as laser cavities, gain mediums, mirrors, output couplers, power sources, and the like are well-known to those skilled in the art and commercially available. Examples are also given in at least some of the incorporated-by-reference citations herein, so further details are not given here.

Also, similarly, software to process acquired raw spectral data, including to distinguish between Raman and non-Raman spectra (non-Raman spectra including background, auto-fluorescence, and other, such as is well-known by those skilled in the art), is well-known in the art and examples given in at least some of the incorporated-by-reference citations herein.

The following examples focus on different ways to generate plural laser wavelengths. It is to be understood they can be utilized with a variety of the available overall system hardware and software for generating, acquiring, and processing spectral signals.

Example 1

In the present invention, multiple-wavelength Raman spectra are collected via a single non-laser diode instrument equipped with a tuning element inside the laser cavity. Examples of this invention are shown in FIGS. 1A-D, in which the laser may be either a gas or solid-state laser, such as are well-known to those skilled in this technology and commercially available from a variety of commercial sources.

Figure 1A:
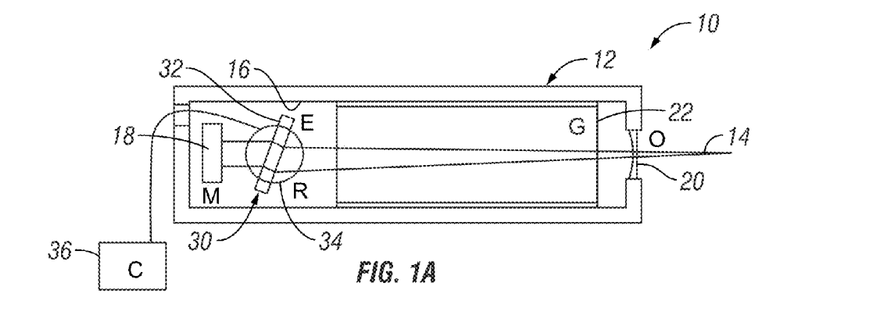
FIGS. 1A and B are top and side views, respectively, of a gas laser with étalon in the cavity on an electrically-controlled rotatable mount according to one exemplary embodiment of the present invention.
Figure 1B:
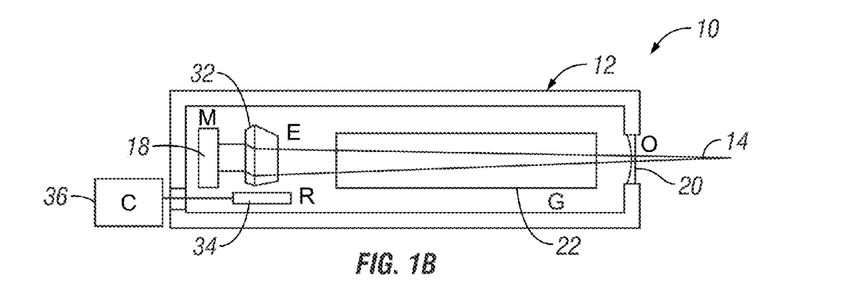

In Figures 1A and B, a first exemplary embodiment of a laser generation instrument 10 includes a conventional laser cavity 12 from which is developed a laser beam 14. As is further typical, the interior 16 of cavity 12 includes a gain medium 22 between a fixed mirror 18 and an output coupler 20 on opposite sides of gain medium 22. By well-known techniques, excitation energy from an energy source (not shown) is applied to gain medium 16. Light energy is produced that basically bounces back and forth between fixed mirror 18 and the mirror component of output coupler/ mirror 20 along an optical path in cavity 12 (generally the path indicated by laser beam 14 in FIGS 1A and B. By appropriate control and selection of components, a particular mode laser beam is allowed to leave cavity 12 through output coupler 20. Beam 14 can be aimed at and impinge on a target.

As can be appreciated, instrument 10 can be mounted in a housing of various form factors, sizes, and materials. In an initial embodiment with an excimer laser, it can be incorporated into a Raman spectroscopy system on a laboratory bench or ruggedized housing for transportability. In another embodiment, it can be man-portable. A user can pick it up with one or two hands and aim it at a target. As such, its size, weight, and form factor are such that it is highly maneuverable and portable, making it applicable to outdoors field work and enclosed space investigations: The materials, construction, and assembly can be selected by the designer. In one example, the housing can be of quite durable and robust materials. Examples are metal, certain plastics, composites, or combinations such as are used to house other technical instruments used in the field. This could include substantial sealing interior components to deter entrance of water, dust, or even gas.

According to one aspect of the invention, a laser tuning subsystem 30 is added inside cavity interior 16. In this embodiment, tuning element or subsystem 30 includes an étalon E or 32 in the cavity on an electrically-controlled rotatable mount 34. Etalon 32 is along the optical axis and between end mirror 18 and gain medium 22. Thus it is intracavity in the sense its form factor can be inserted inside a typical laser cavity interior 16 and moveably adjusted. As would be appreciated by those skilled in the art, it is possible that aspects of practicality may require some reconstruction or reconfiguration of an existing laser cavity to accommodate one or more of the exemplary tunable designs. In some cases, however, they may be retrofitable. Figures 1A and B also diagrammatically illustrate that rotatable mount 34 is electrically connected to a controller 36. This can be outside cavity 12, but it could be, if desired, built into a portable housing of cavity 12.

By principles of physics well-known to those familiar with etalons, adjustment of its angle of orientation to the optical axis in laser cavity 12 can result in change in output wavelength of the laser from output coupling 20. See, e.g., "Lasers" by Anthony E. Siegman, chapters 11 and 13. © 1986, University Science Books, Sausalito, Calif., ISBN 0-935702-11-3(U.S.), incorporated by reference herein. See also U.S. Pat. No. 4,081,760, incorporated by reference herein. The make-up and characteristics of etalon 32 can be selected by the designer. For example, etalon 32 and its range of angular adjustment by rotation can be selected to generate at least two different laser output wavelengths. This can be any difference in wavelength. But generally it is beneficial to have more than minute separation. One example of non-minute is on the order of one FWHM (full-width at half maximum) of a typical Raman feature. It is presently believed that between on the order of ¼ FWHM to 2 or 3 times FWHM would be one possible range. But the invention is not so limited. The ability to achieve this can depend on the construction of etalon 32 and the range of rotation of etalon 32.

The etalon (for example a plane parallel plate etalon) is essentially a resonator having a resonant wavelength. Angle of the etalon relative to the optical path between end mirror and output coupler in the laser cavity is one variable that determines the resonance wavelength of the etalon. Therefore, rotation of the etalon can change the laser wavelength. In other words, the angle of the etalon can select the laser wavelength and, thus, can tune the laser.

Figure 1C:
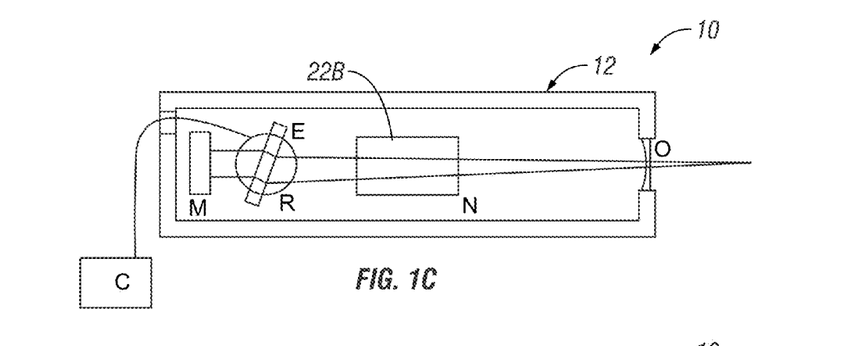
FIGS. 1C and D are similar but solid-state laser with an étalon in the laser cavity. Letters are as follows: E=étalon, G=gas breakdown grid, M=mirror, O=output coupler, N=solid-state laser with possible Q-switch, and R=rotating mount. The triangular feature protruding through the output coupler is a ray diagram of laser light.

In contrast, FIGS. 1C and D differ from FIGS. 1A and B in that it is applied to a solid-state laser with étalon 32 in the laser cavity 12, again between end mirror 18 and gain medium 22 along the optical path. As can be seen, again etalon 32 and its rotatable actuator 34 are fitted intracavity into cavity 12. In all FIGS. 1A-D, letters refer to the following: E=étalon, G=gas breakdown grid, M=mirror, O=output coupler, N=solid-state laser with possible Q-switch, and R=rotating mount. The triangular feature protruding through the output coupler is a ray diagram of laser light.

Further discussion of the gas laser embodiment and the solid state laser embodiment follow.

In the first implementation (FIGS. 1A and 1B), the tuning element 30 is an étalon that is capable of changing the laser wavelength over the gain bandwidth of the laser. The gain bandwidth of the laser itself preferably is larger than the desired range of tuning. For instance, in a KrF excimer laser, the gain bandwidth may be 300 pm or more. The étalon is tuned, for instance, by rotating it inside the cavity via a piezoelectrically-controlled rotation stage or similar device that can be synchronized with Raman spectral collection hardware. One such device has been described in U.S. Pat. No. 5,331,651 and is incorporated by reference herein, and is intended for the tuning of a semiconductor or other external cavity laser.

As can be appreciated by those skilled in the art, rotational actuator 34 and its controller 36 can be any of a variety of types. A number of commercially-available rotational stages, such as are used with microscopy or other technologies can be used and set-up to achieve needed rotational accuracy and range for etalon 32. One subtle but important feature of embodiments according to the invention is that extreme precision and accuracy of rotation is not necessarily required to effective operation. In other words, cost, complexity, and resources can be avoided by having reasonable control of rotational position of etalon 32 in cavity 12, not absolute or extremely fine control or knowledge of position. What is important is the ability to at least roughly change rotational position of the etalon to effectuate more than a minute difference in laser wavelength. Processing software keys on the separating of Raman spectra from non-Raman spectra depending not so much on how specific its knowledge of laser wavelength differences, but rather that two meaningfully spaced wavelengths are produced. At least some software useable with the system keys on the fact that non-Raman spectra do not vary much with small changes in laser wavelength, while Raman spectra do. Therefore, it is the ability to recognize this relative phenomena allows good separation of Raman data from non-Raman, not precise and accurate information about the different wavelengths or how they are created.

Therefore, the type, control, and assembly of the rotational stages 34 and controller 36 can be less stringent than might be indicated. This is a meaningful, but subtle advantage of the present invention. In these embodiments, the adjustment of the etalon rotationally can be controlled in the range of 0.05 degrees. The speed from home to a second position can be on the order of 100 msec. Any lag in time to switch between rotational positions caused by controller 36 and friction or the like would be minimized. This would be similar for movement to then third, fourth, etc. positions. The typical maximum range of rotation would be 0 to 0.5 degrees from home (e.g. a first state). As will be appreciated by those skilled in the art, the foregoing values can be relative to certain assumptions. For example, those specific values assume 500 Hz repetition rate and single pulse switching which would inform a 1ms switching rate. An ideal rotational mount would achieve 0.5° rotation with 1% error in this time frame. If this cannot be achieved, a possible alternative piezoelectric rotation stage would be a Newport Agilis CONEX-AG-PR100P, commercially available, which should take 250 ms to make the rotation. This would require an intelligent gating approach as described herein. Alternatives are, of course, possible. Some examples of rotational stages are U.S. Pat. Nos. 6,486,574, 6,917,420, and 8,554,344, which are incorporated by reference herein. The designer would have to account for the operational parameters of such a translation member (which is some of the exemplary embodiments would be linear translations instead of rotational translation).

Figure 1D:
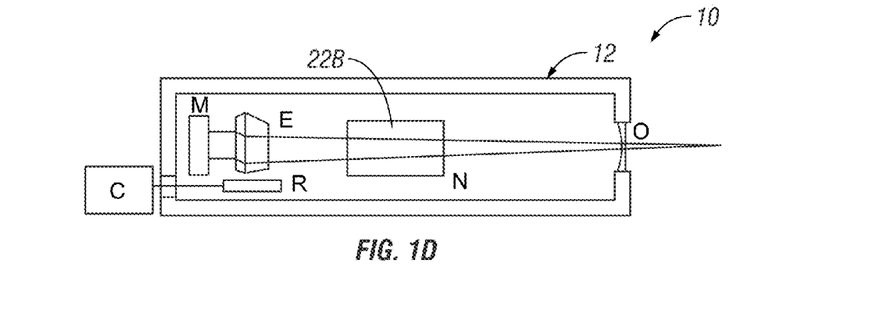

In another implementation with the same angle-tuning of an étalon, a solid-state laser such as an Nd:YAG, which has a typical gain bandwidth of 600 pm is used. This is shown in FIGS. 1C and 1D.

Other methods of wavelength tuning are possible, such as varying the étalon spacing via thermal or mechanical means. Additionally, the wavelength can be selected or tuned by using optical transmission or reflection gratings inside the laser cavity. Examples of varying étalon spacing via thermal or mechanical means are known in the art in different contexts, but could be applied here. Optical transmission or reflection grating modifications are also known in the art in different contexts but could be applied here.

Thus, it can be seen how the embodiments of Example 1 allow economically, compact, even retrofittable selectable switching between two laser wavelength states by simple control of a single rotatable etalon in the laser cavity. State 1 is an outputted laser at a first wavelength. State 2 is an outputted laser at a second wavelength. As indicated, by appropriate design, the difference in wavelengths of State 1 and 2 can be more than minute. One example is at least ¼ FWHM difference. But it could be, and for many applications might be beneficial to be 1 FWHM or 2 FWHM. But it could be more or less. Also, the addition of laser tuning does not involve material alteration of the line-narrowing components or elements of the instrument. The form factor of the etalon and rotational stage fit within the general confines of the cavity. One example, but not limited to, is an etalon of approximately 1 inch diameter by 2 inches long, and rotational stage of 2 inch by 2 inch by 0.75 inch, for a laser cavity and enclosure of approximately 18 inch by 5 inch by 5 inch internal dimensions. Of course, a variety of cavity sizes exist and, thus, the designer can select laser tuning components accordingly. Those skilled in the art would balance needed design factors according to need or desire.

Example 2

Figure 2A:
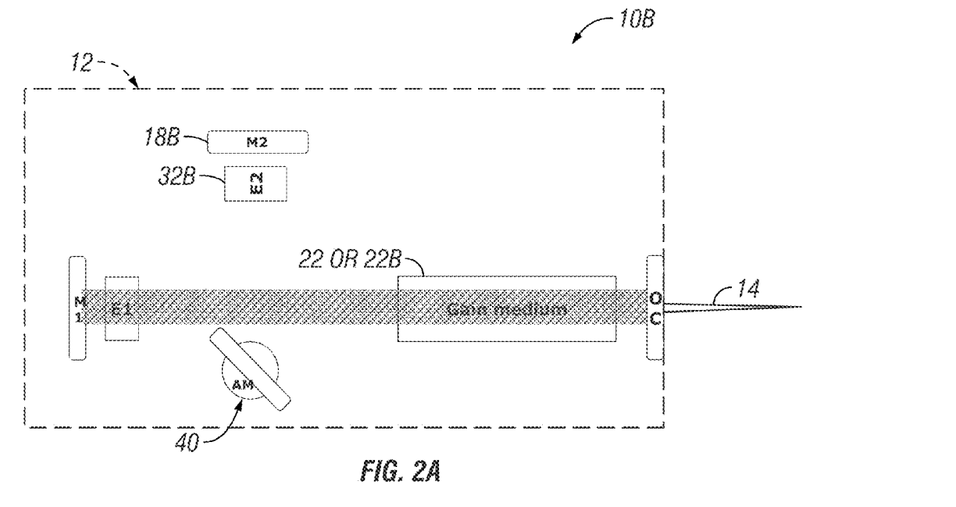
FIGS. 2A and B is a schematic view of a laser with a switching element between two cavity end mirrors and two étalon according to one aspect of the invention. In this implementation, the laser gain medium can be solid-state or gas. AM is the modulator that switches the cavity. M1 and E1 correspond to cavity 1, emitting wavelength 1, in FIG. 2A. M2 and E2 correspond to cavity 2, and emit wavelength 2 when the adjustable mirror is in the cavity path, as shown in FIG. 2B.

An additional implementation, shown in FIGS. 2A and B, utilizes a modulator 40 to rapidly switch between two laser cavity end mirrors 18 and 18B with line narrowing elements, such as an étalon 32 and 3213 associated with each end mirror 18 and 18B. Instead of interposing a switchable or controllable element along a single optical path, as in FIGS. 1A-D, this embodiment. instead essentially switches between two alternative optical path sections between a cavity end mirror and the gain medium. The first optical path section (between gain element 22 and mirror 18/etalon 32) is basically like in FIGS. 1A-D. The components would be selected and configured to generate a first state or laser output wavelength. The modulator 40 would be actuated to a position outside the optical path.

Figure 2B:
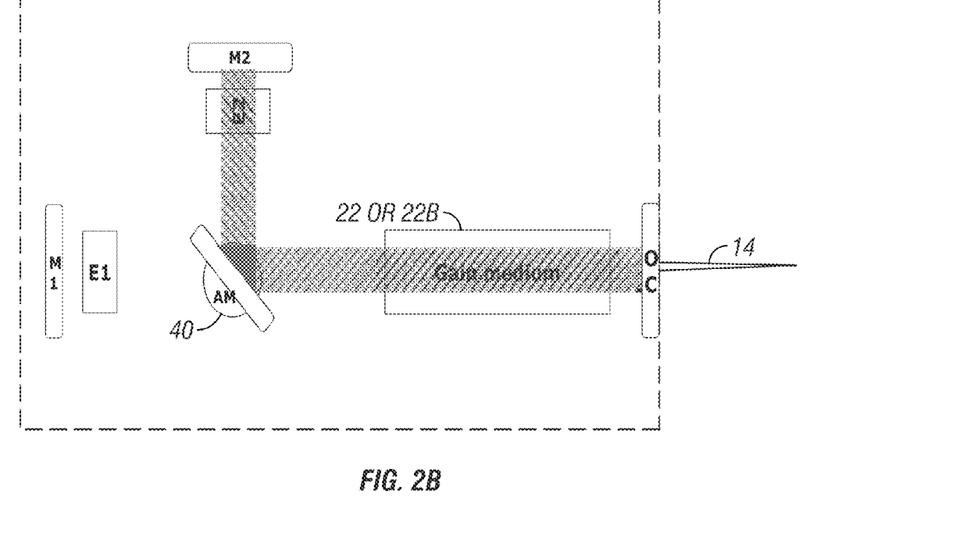

The second state, generating a second laser output wavelength, is effectuated by movement of modulator 40 into the optical path. This intercepts the laser energy and diverts it to the alternative optical path section (to end mirror 18B and etalon 32B). Those components would be designed and configured to cooperate with gain medium 22 to produce a different laser output wavelength. This can be by a different angle of etalon 32B, a different etalon 32B, or other difference from etalon 32, or by diffraction or transmission grating. Those skilled in the art are familiar with such components.

FIGS. 2A and B diagrammatically illustrate second mirror 1813 and second etalon 32B orthogonal to the optical path from gain medium 22 to first mirror 18 and etalon 32. If modulator 40 is a mirror, it could be set to a fixed 45 degree angle relative to the optical path in FIG. 2A so that when translated into position in FIG. 2B, it would reflect the laser energy at 90 degrees to etalon 32B and mirror 18B. But other angular orientations are possible with appropriate redirection from modulator 40. As with rotational stages, actuators to translate modulator 40 in a linear fashion are commercially available. Examples in microscopy (linear stages) with minute control, are well-known. Hardware to control them is also. Such can be effectively integrated into a laser cavity. As can be appreciated, this embodiment does change the form factor of the laser cavity. However, the physical size of such added optical path section to etalon 32B and mirror 16B, and the size of such added components, can still be effectuated in a relatively compact and portable housing 12.

The modulator in FIGS. 2A-B may be a motorized mirror, acousto-optic device, Pockels cell, pentaprism, or other modulating technology. Each line-narrowing element is tuned to a slightly different wavelength that falls within the laser gain medium, allowing rapid changing of wavelength without adjusting the line-narrowing element. The switching between states can be on the order of 1 Hz to 100 MHz, which is achievable with commercially available devices; the speed and frequency of switching being dependent on the type of modulator chosen. It will be appreciated that these design factors will be selected according to need or desire of the application and system.

Figure 3A:
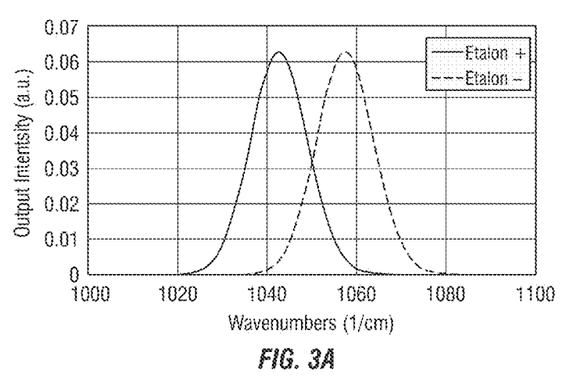
FIGS. 3A-C are graphed examples of intensity versus laser wavelength (expressed in wavenumbers) for the laser output as the étalon is tuned between two positions.
Figure 3B:
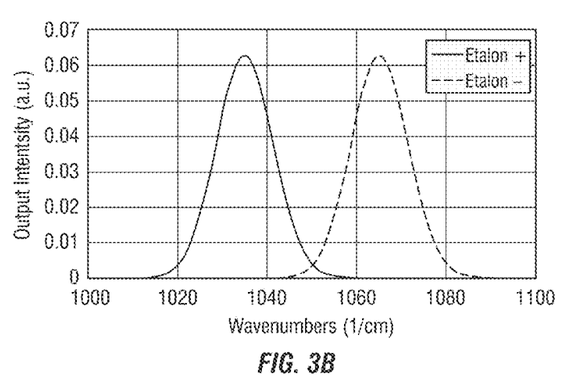
Figure 3C:
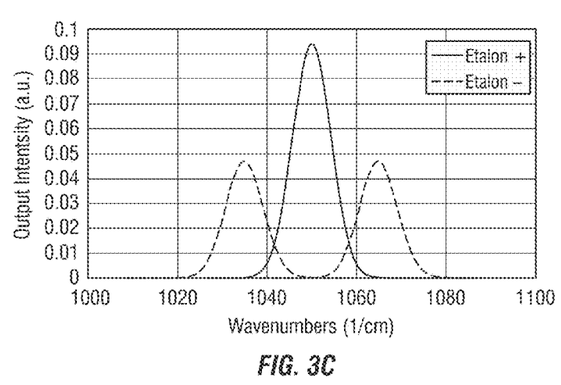

In these implementations (as with those of FIGS. 1A-D), the changing of the laser wavelength results in Raman spectra that are collected at two or more laser wavelengths separated by some spacing such as one, two, or more times the fill-width at half maximum (FWHM) of a typical Raman feature (see illustration of FIGS. 3A-C). If two excitation wavelengths are used, as shown in FIGS. 3A and B, we estimate that one-fourth the typical Raman FWHM for the sample is a practical minimum spacing to receive benefits, with the most benefit likely to occur at a wavelength spacing near two times the FWHM. If more than two excitation wavelengths are used, the spacing between the wavelengths can be equal or unequal. One possible implementation with three excitation wavelengths, uses two wavelengths emitted simultaneously from the same étalon that have the same integrated intensity as the third wavelength. The two simultaneous wavelengths can bracket the third wavelength, while the fluorescence background remains constant. This is illustrated in FIG. 3C. It is to be understood, however, that variations are possible, even outside the range indicated above. As will be appreciated by those skilled in the art, the wavelength output of a pulsed or cw laser can be changed by alternating between two different cavities, each one with a different étalon and fixed end mirror. However, alternatives such as moveable mirrors or pentaprisms that select which cavity in associated wavelength are also possible in this example and other examples described herein.

Example 3

In addition to the hardware configurations of Examples 1 and 2, the following hardware configurations are also envisioned for implementing intracavity laser tuning with or without the signal processing concepts discussed immediately above.

Figure 4:
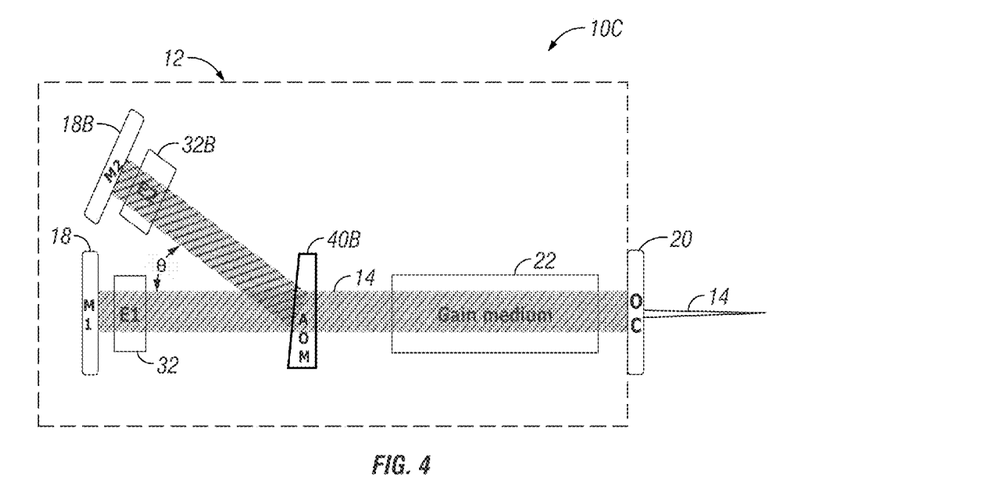
FIG. 4 is a diagrammatic view of an acousto-optically modulated laser implementation according to an alternative embodiment of the invention. Energizing the modulator (AOM) refracts the light and switches from the M1 E1 cavity to the M2 E2 cavity, changing the wavelength.

An acousto-optic modulator 40B is used to refract the cavity by an angle, theta or θ, allowing for rapid switching of wavelength by selecting a different narrowed cavity. (See FIG. 4). Such modulators are commercially available. One is discussed in G. D. Baldwin, Output power calculations for a continuously pumped Q-switched YAG:Nd$^{3+}$ laser, IEEE J. Quantum Electronics, QE-7, 715, 1971, which is incorporated by reference herein. This is a variation on allowing switching between two laser wavelength states. The basic principle of such modulators uses the acousto-optic effect to diffract and shift the frequency of light using sound waves (e.g. at radio frequency). One configuration uses a piezoelectric transducer attached to a material (e.g. glass) and an oscillating electric signal drives the transducer to vibrate. This creates sound waves in the glass that change the index of refraction. Incoming light scatters off the resulting periodic index modulation and interference occurs similar to Bragg diffraction. The designer can program a controller to control the amount of index of refraction change.

Example 4

Another hardware configuration for controllable switching between two states of laser output wavelength is as follows.

Figure 5:
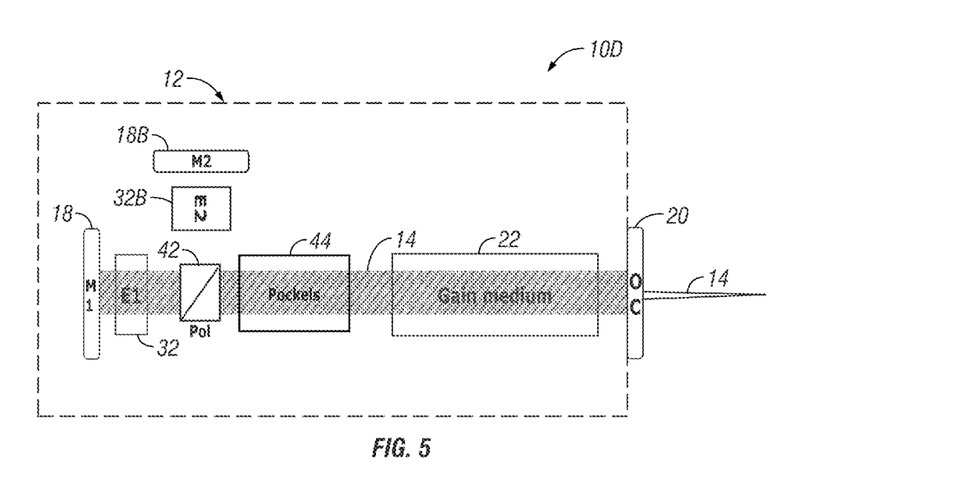
FIG. 5 is a diagrammatic view of a Pockels cell modulated laser cavity for SERDS according to another exemplary embodiment of the invention. Switching the Pockels cell changes the allowed polarization of light and the wavelength. Cavity 1, with M1 and E1 has polarization 1 and wavelength 1. Cavity 2, with M2 and E2 has polarization 2 and wavelength 2.

High speed, solid state wavelength switching is accomplished via a Pockels cell 44 and polarizer 42. When the Pockels cell is deenergized, the laser gain builds in cavity 1 (the optical path between output coupler 20 and mirror 18/etalon 32) with polarization 1 and wavelength 1. Energizing the Pockels cell results in only polarization 2 being generated in cavity 2 (the alternative optical path between output coupler 20 and mirror 18B/etalon 32B) at wavelength 2, which is orthogonal to cavity 1. (see FIG. 5). Pockels cells and polarizers are well-known and commercially available. An example is discussed in Norman Hodgson and Horst Weber, Laser resonators and beam propagation: Fundamentals, advanced concepts and applications, and J. Junghans, M. Keller, H. Weber, Laser resonators with polarizing elements—eigenstates and eigenvalues of polarization, Applied Optics, 13, 2793, 1974, incorporated by reference herein. The Pockels effect relates to birefringence in an optical medium induced by a constant or varying electric filed. They are sometimes referred to as voltage-controlled wave plates. Essentially it can function as a fast shutter capable of opening and closing in nanoseconds. It has no moving parts, can be of a form factor that can be built into the laser cavity, and therefore can have benefits according to aspects of the invention.

One example of a birefringent device is a crystal (e.g. of KDP) which splits a beam of polarized radiation, incident under Brewster angle. Rotating the device while keeping the angle of incidence at the Brewster angle changes the direction of the optical axis relative to the direction of electric field vector changes, leading to changes of wavelength.

Example 5—Electronic Signal Timing Techniques

As indicated above, the embodiments can be implemented with a variety of laser types. This includes pulsed or continuous wave (CW) lasers. Embodiments of the invention can benefit from specific control of laser generation and signal acquisition. Some examples are discussed below in the context of a pulsed laser.

Figure 6A:
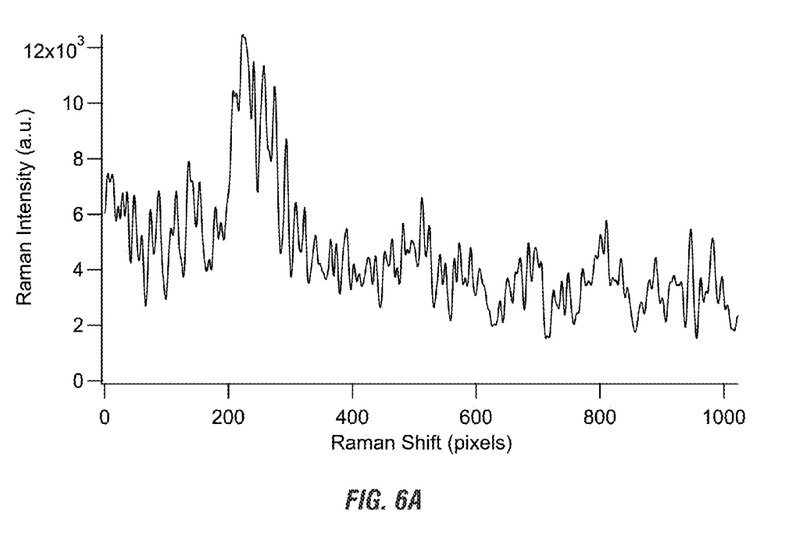
FIG. 6A is a graphed example of two second Raman data at one wavelength.
Figure 6B:
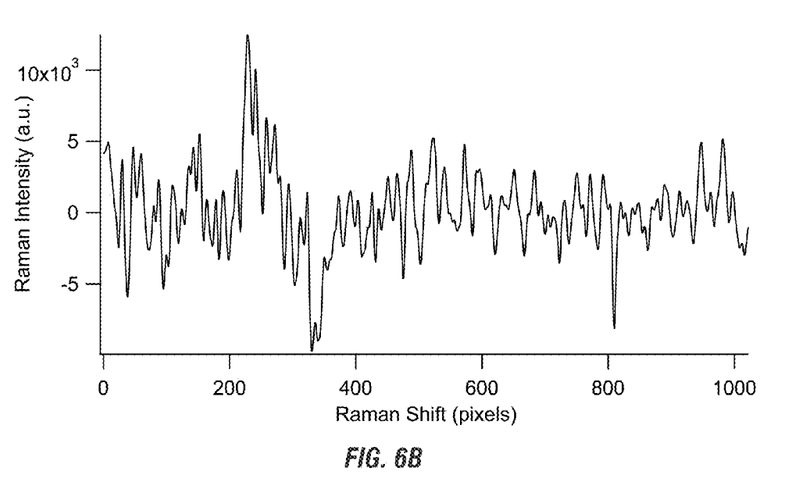
FIG. 6B is a difference spectrum of one second Raman data at wavelength 1 and wavelength 2.
Figure 7:
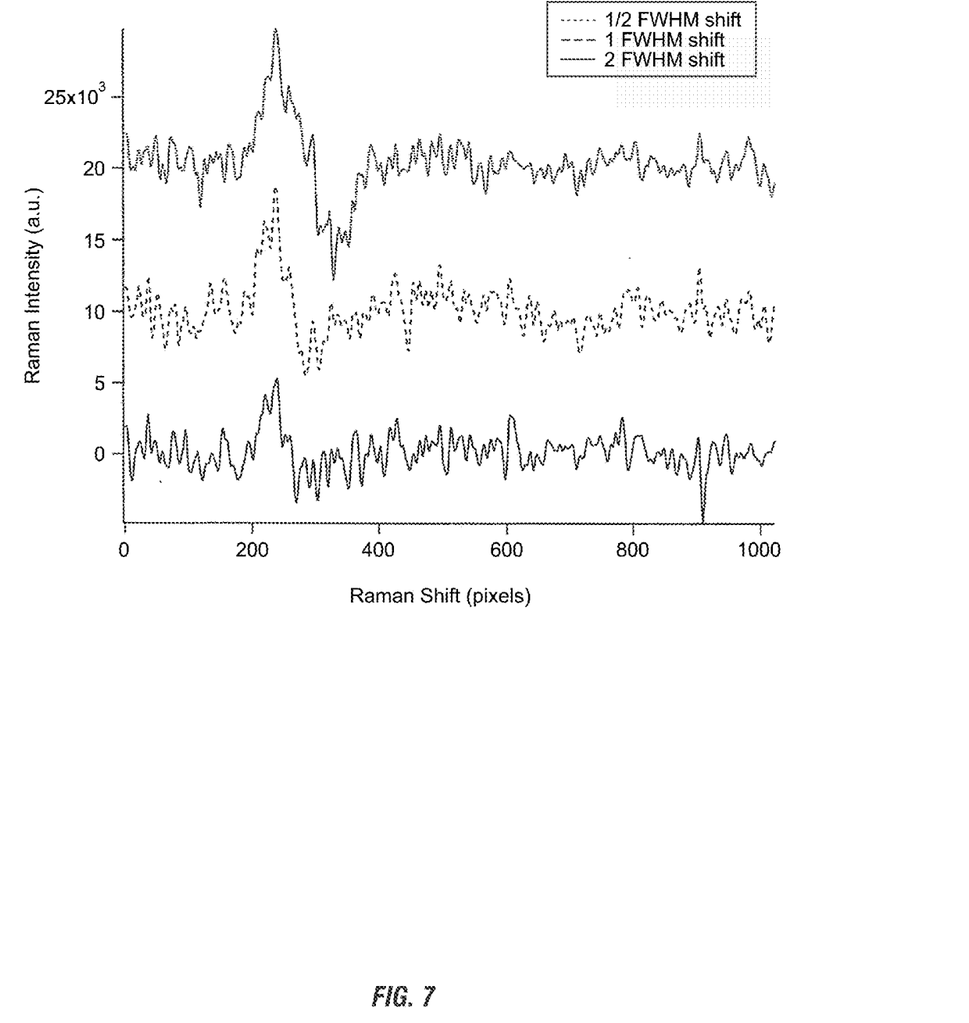
FIG. 7 is the graphed example of Raman difference spectra of the $NO_3^-$(ss) mode in aqueous solution with sodium fluorescein dye. The bottom trace is the difference spectrum of two laser emission wavelengths at ½ FWHM apart. Similarly, the middle trace is a difference spectrum at 1 FWHM apart, The top trace is for 2 FWHM separation.

FIGS. 6A-B and 7 show examples of Raman data collected from a dilute aqueous solution of ammonium nitrate and fluorescein dye; the excitation wavelength is near 391 nm via a YAG pumped dye laser. The data is shown in pixel space with the 1040 $cm^{+1}$ nitrate band near pixel 200. FIG. 6A shows two seconds of Raman data; it is clear that there is a high baseline due to background fluorescence. FIG. 6B is the difference spectrum of a single one second Raman acquisition at wavelength 1 and a one second spectrum collected at wavelength 2, approximately two FWI-IM from the first wavelength. The difference spectrum compensates for the intensity of the background, and yields and differential shaped peak. This differential can be easily detected by an array of numerical methods. FIG. 7 shows the effect of tuning the excitation wavelength from one-half FWHM to two FWHMs in wavelength space on difference spectra. Even at one-half FWHM wavelength separation, the background is compensated for and the characteristic differential shape is present. At one and two FWHM, significantly enhanced feature identification is possible.

Once Raman spectra are collected, they are processed via an algorithm to differentiate the non-Raman background, such as fluorescence, from the Raman spectrum, based on the peak width and differences between the spectra. The non-Raman background includes spectral features which do not vary significantly in intensity or wavelength due to small changes in the laser excitation wavelength. This can result in suppression of non-Raman background in a Raman spectrum or alternately suppression of Raman features if desired.

Implementation of the scheme may for instance be accomplished by switching the étalon angle between two or more target angles using a rotation stage or piezoelectric element. Some variation in actual étalon angle near the target angles is expected due to mechanical variations such as wear and temperature. The variations may be small enough to not require any extra effort, or may be larger in which case additional data processing may be needed to correctly interpret spectra. We envision several possible embodiments of this:

(1) Using a piezoelectric element, the étalon is mounted such that when the piezoelectric element is not energized, the étalon angle is held near some fixed angle by tension, compression, or torsion. The étalon angle is held near some other fixed angle when the piezoelectric element is energized, for instance by pressure of the piezoelectric element pressing some portion of the étalon assembly against a hard stop. In another embodiment using a motor, the étalon angle is adjusted by changing the motor position. Other embodiments may use hydraulic, pneumatic, electrostatic, or magnetic means of adjusting the angle.

(2) The étalon angle is varied continuously through some controlled motion using a mechanical, piezoelectric, acoustic, hydraulic, pneumatic, electrostatic, or magnetic actuator.

Figure 8:
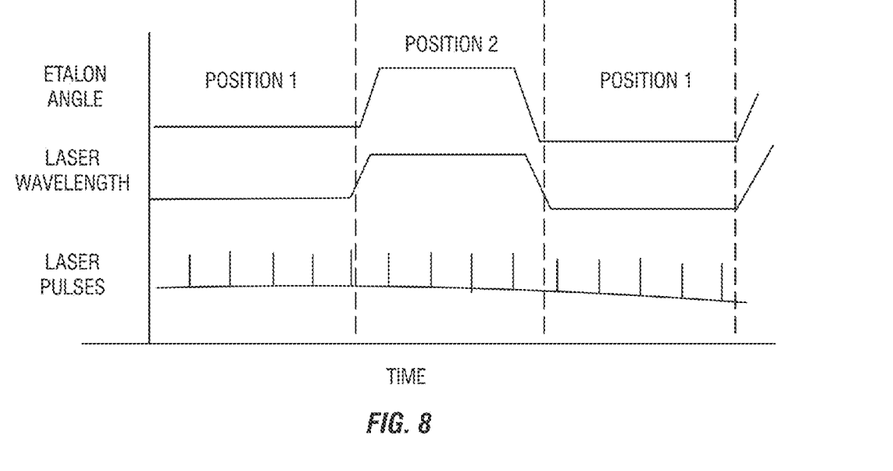
FIG. 8 is a graphic representation of pulsed laser timing with two laser wavelengths.

(3) Using a pulsed laser, the étalon is switched between two angles with motion synchronized in such a way that some number (N) of laser pulses occur with the étalon in one position (first wavelength) and then some number (M) of laser pulses occur with the étalon in the other position (second wavelength). The values of N and M may be the same or different. N=M=1 is one possibility. Another possibility is that N>1 and M>1. (FIG. 8)

The spectral acquisition is synchronized with the étalon motion such that light collected from a particular laser pulse can be associated during data processing with the étalon angle or laser wavelength for that pulse. This can be done for instance by alternating between two or more spectral accumulation buffers in sync with the étalon angle change, or by separately recording data for every pulse and associating that data with the appropriate angle, or by recording data for N pulses in a spectral accumulation buffer and recording the buffer and then recording data for M pulses in a spectral accumulation buffer and recording that buffer. Other spectral readout schemes are obvious to a practitioner skilled in the art.

The values of N and M for the pulsed laser need not be fixed. They can be adjusted to change duty cycle N/(N+M) or period (N+M).

In a more general embodiment, there are more than two target étalon angles. A number of laser pulses N1 is collected at one angle, followed by a number N2 at a different angle, followed by still another number N3 at still another angle, etc. The angle can be changed following some scheme such that all angles are selected sequentially or can follow a more complex scheme, so long as the étalon angle selection is synchronized with the spectral. data collection and the data collected from laser pulses at any given angle can be associated with that angle.

Figure 9:
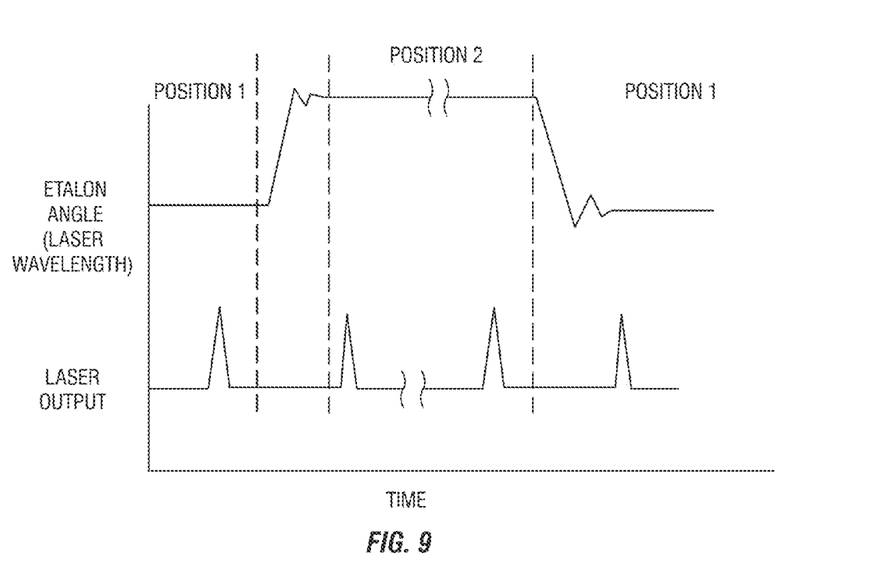
FIG. 9 is a graphic representation of rapidly switched étalon timing.

If the time required to switch between wavelengths is small compared to the time between laser pulses, the switching may be synchronized such that all laser pulses occur when the étalon is near a target angle. (FIG. 9)

Figure 10:
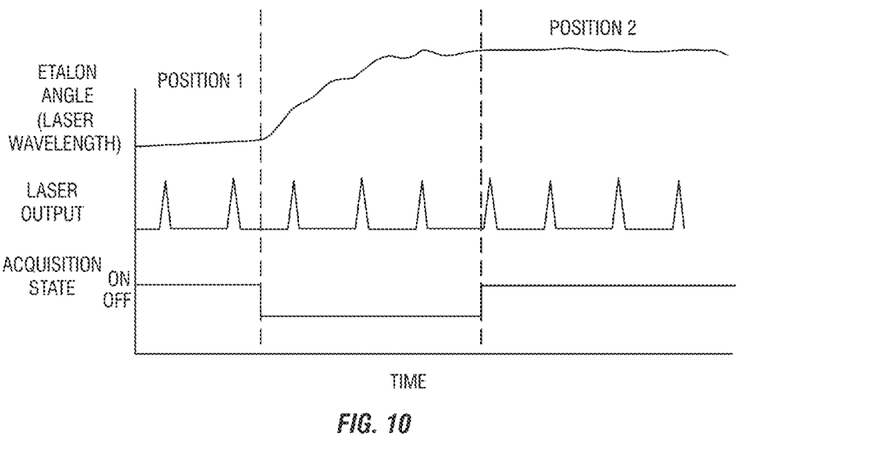
FIG. 10 is a graphic representation of slowly switched étalon timing.

If the time required to switch between wavelengths is similar to or larger than the time between laser pulses, one or more laser pulses may be generated at wavelengths not close to a target wavelength. In this case, light generated for these pulses may be excluded from the collected spectra by appropriately gating the data acquisition system using any of several well-known methods. (FIG. 10)

Figure 11:
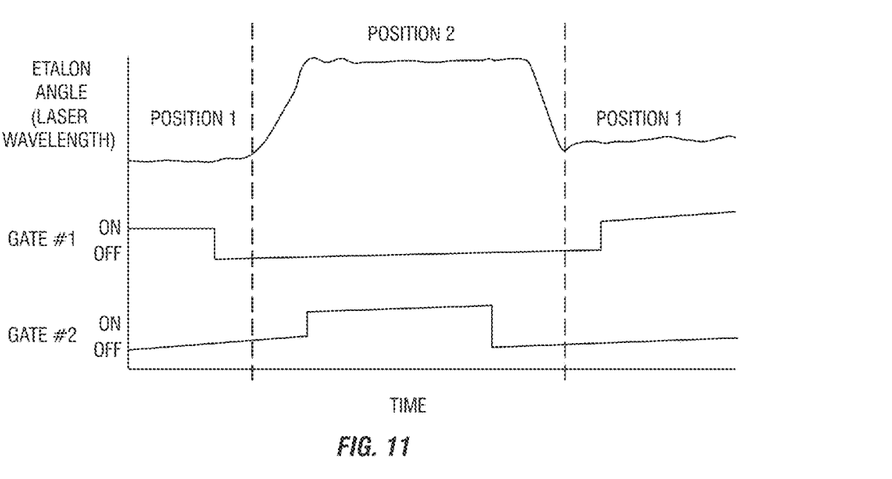
FIG. 11 is a graphic representation of continuous wave (CW) laser with acquisition gating.

(4) Using a continuous wave (CW) laser, the étalon is similarly switched between two or more angles. In one embodiment of this, the étalon angle is switched relatively quickly, so that the étalon is generally nearly stationary near one or another target angle. For this application, the étalon angle control may be synchronized with spectral acquisition such that the light collected when the étalon angle is not within some acceptable tolerance of a target angle is rejected, for instance by electrically or mechanically gating the spectrometer using any of several well-known methods. (FIG. 11)

Figure 12:
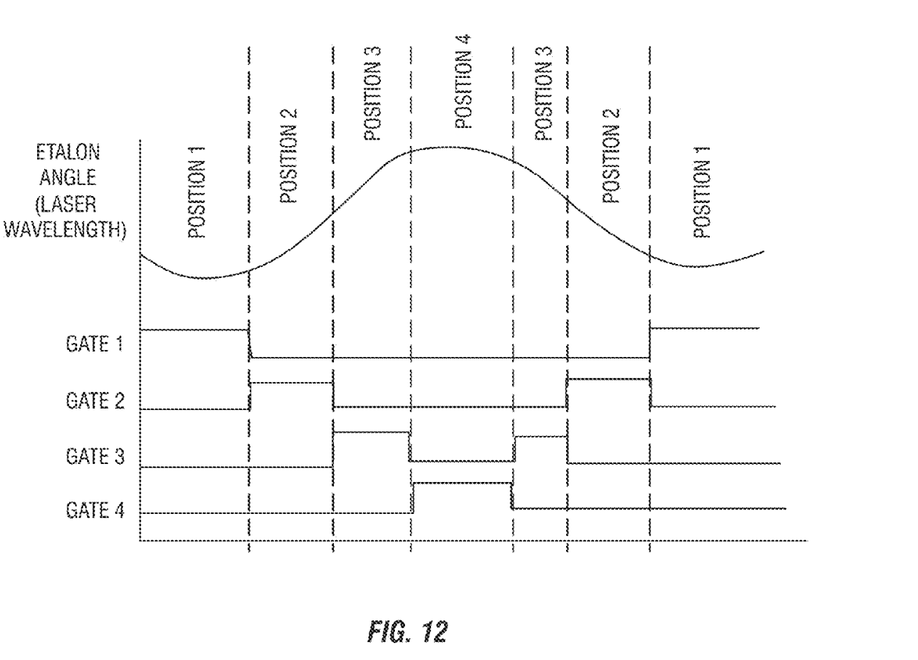
FIG. 12 is a graphic representation of CW laser with smoothly changing wavelength.

(5) Using a CW laser, the étalon angle is adjusted using some smoothly varying motion such as a sinusoid. Data acquisition is synchronized with the angle adjustment. (FIG. 12)

(6) The wavelength output of a pulsed or CW laser is changed by alternating between two different cavities, each one with a different étalon and fixed end mirror. The alternation is provided by a moveable mirror or pentaprism that selects which cavity and associated wavelength will build gain. (FIGS. 2A and B).

Options and Alternatives

The invention can take a variety of forms and embodiments. Variations obvious to those skilled in the art will be included within the invention, which is not limited by the embodiments discussed herein but rather defined by the claims appended hereafter.

Some alternatives have been mentioned above. Again, materials, form factors, operating parameters, and the like can vary according to need or desire.

An alternative to an angle-changeable etalon is a grating. One example is a an Echelette grating. Rotation of the grating changes the wavelength of the backward diffracted radiation and thus the laser wavelength from the cavity.

Another alternative embodiment uses two spinning reflector end mirrors are used to switch cavities in a pulsed YAG laser. The spinning reflectors are set to rotate such that pulses or pulse trains alternate between wavelengths. The reflectors are synchronized to each other and the pump source via a lock-in-amplifier. When one mirror is facing the cavity and is synchronized with the cavity excitation, gain builds up along that cavity, resulting in emission at wavelength 1. As the next mirror synchronizes with the excitation pulse, emission from the second cavity at wavelength 2 occurs. Such an arrangement could be configured similar to FIG. 2B but with a polarizer in place of translatable mirror 40 and with mirrors M1 and M2comprising rotating reflectors, which can be prisms or mirrors. This is a variation on the spinning mirror Q-switch, which is well-known technology in the art. Examples of rotating reflectors can be seen in U.S. Pat. Nos. 3,548,337 and 3,769,608, and incorporated by reference herein.

It can therefore be seen that the exemplary embodiments all are linked by ways in which the laser wavelength for interrogating a target or sample for acquisition of Raman spectra can be effectively varied between at least two states— a first laser wavelength and at least one different laser wavelength.

For all these embodiments, precise and accurate knowledge of the étalon angle and/or the laser wavelength is not needed if certain additional precautions are followed. Variations about the target angles (or equivalently, laser wavelength) may be ignored if the magnitude of the laser wavelength variations is small compared to the typical feature width of the Raman spectrum. If significant variations occur,' the variation can be accounted for using well known calibration techniques such as directly measuring the laser wavelength or measuring the spectral position of known Raman features.

Once aligned, the Raman features will be mostly constant allowing them to be extracted from multiple spectra via principal component analysis or by finding spectral channels with standard deviation relative to the mean below a threshold. Other processing techniques, such as those commonly described in the literature for use in Shifted-Excitation Raman Difference Spectroscopy (SERI)S) may also be used as desired or necessary. See, e.g., I, Osticioli, A. Zoppi, and E. M. Castellucci, "Shift-Excitation Raman Difference Spectroscopy?Difference Deconvolution Method for the Luminescence Background Rejection from Raman Spectra of Solid Samples," *Appl. Speclrosc.*, vol. 61, no. 8, pp. 839-844, 2007, cited above and incorporated by reference herein.

As can be appreciated, the examples of the invention would be combined with other appropriate components to form a complete system.. An example of some of those components for a detector and a spectograph effective for the purpose herein can be seen at U.S. Pat. No. 7,864,311, incorporated by reference herein, and some of the other cited references.

An additional exmaple for tuning the laser could comprise mechanically changing the spacing between parallel plates of an étalon. Some sort of piezoelectric actuator would be effective for this purpose. Such linear translators are commercially available and known in the art.

What is claimed is:

1. A method of Raman spectroscopy for non-destructive interrogation of solids, liquids, solutions, or mixtures chemical detection in an integrated compact instrument with improved gain bandwidth at stand-off distances comprising:
   a. operating a single non-diode, pulsed laser having a gain medium at a first wavelength;
   b. directing the laser at the first wavelength onto a target sample;
   c. collecting scattered or excited light from the target sample across a spectral range during operation of the laser at the first wavelength;
   d. operating the laser at a second wavelength, the second wavelength offset a pre-designed amount from the first wavelength with a tuning element inside a laser cavity, wherein the tuning element comprises:
      1. an intracavity etalon having an adjustably controllable pathlength to produce different laser wavelenghts; and
      2. an acutator connected to the etalon to change the angle of the etalon relative the optical path, the actuator having an interface for operative connection to a controller that can instruct rotation amount, speed, and direction of the etalon; wherein the actuator comprises a rotational stage or piezoelectric motor that can adjust (a) the angle of the etalon relative the optical path over a range at submicron increments or, (b) distance between etalon parallel plates;
e. collecting scattered or excited light from the target sample across the spectral range during operation of the laser at the second wavelength;
f. detecting differences between the collected spectra at the first and second wavelengths to separate Raman spectra from non-Raman spectra; and
g. using teh separated Raman spectra for Raman spectroscopy purposes wherein pulsed laser generation is synchronized withe spectral acquisition to promote Raman spectral extraction and analysis, and the laster generation and spectral acquisition is combined in a fixed or portable instrument;
h. wherein the controller is programmable for controlling the tuning element and includes software that controls one or more of:
  1. swithcing between first and second states;
  2. speed of switching;
  3. length of time in either first or second state;
  4. correlation between type of laser and acquisition; and
  5. synchronization with laser generation and spectral signal acquisition
g. further comprising one or more of:
  1. filtering of raw spectral information;
  2. gating of raw spectral information;
  3. comparision of Ram spectra at multiple laser wavelengths;
  4. identifying know materials in the Raman spectra; and
  5. idenifying unknown materials in the Raman spectra.

2. The method of claim 1 further comprising:
a. operatively connecting to an excitation source for the gain medium to generate the laser and to a Raman spectroscopy processing subsystem for acquiring raw spectral data from a sample interrogated by the laser and separating Raman spectra from the raw data;
b. producing line narrowing laser output;
c. tuning the laser comprising:
  i. the first state which produces a laser from an output coupler at the first wavelength; and
  ii. the second state which produces a laser from the output coupler at the second wavelength;
  iii. wherein the first and second wavelengths are within the gain bandwidth of the gain medium;
d. so that the intracavity laser tuning subsystem can be used to generate plural laser wavelengths which can be used to acquire multiwavelength Raman spectra for evaluation in a processing subsystem without having to change the line narrowing elements of the instrument.

3. The method of claim 1 wherein the first and second wavelengths comprise multiple wavelengths wherein at least two laser wavelengths are spaced at full-width at half maximum (FWHM) or a fraction or multiple thereof.

4. The method of claim 3 wherein the multiple wavelengths comprise more than two wavelengths and spacing between wavelengths is equal or unequal.

5. The method of claim 1 further comprising processing collected data to isolated non-Raman background based on peak changes between the data at multiple wavelengths.

6. The method of claim 1 wherein the tuning element is tuned, the tuning comprising switching between two or more wavelengths with the actuating component.

7. The method of claim 6 wherein the tuning comprises switching between two or more wavelengths with motion synchronized such that number (N) of laser pulses at a first wavelength position differs from number of laser pulses at a second wavelength position.

* * * * *

UNITED STATES PATENT AND TRADEMARK OFFICE
CERTIFICATE OF CORRECTION

| | |
|---|---|
| PATENT NO. | : 9,905,990 B1 |
| APPLICATION NO. | : 14/689964 |
| DATED | : February 27, 2018 |
| INVENTOR(S) | : Pohl et al. |

It is certified that error appears in the above-identified patent and that said Letters Patent is hereby corrected as shown below:

In the Claims

In Column 14, Claim 1, Line 65:
DELETE "lenghts"
INSERT --lengths--

In Column 14, Claim 1, Line 66:
DELETE "acutator"
INSERT --actuator--

In Column 15, Claim 1, Line 15:
DELETE "teh"
INSERT --the--

In Column 15, Claim 1, Line 17:
DELETE "withe"
INSERT --with--

In Column 15, Claim 1, Line 18:
DELETE "laster"
INSERT --laser--

In Column 15, Claim 1, Line 24:
DELETE "swithcing"
INSERT --switching--

In Column 15, Claim 1, Line 34:
DELETE "comparision" and "Ram"
INSERT --comparison-- and --Raman--

Signed and Sealed this
Twenty-second Day of May, 2018

Andrei Iancu
*Director of the United States Patent and Trademark Office*

CERTIFICATE OF CORRECTION (continued)
U.S. Pat. No. 9,905,990 B1

<u>In Column 15, Claim 1, Line 36</u>:
DELETE "know"
INSERT --known--

<u>In Column 15, Claim 1, Line 38</u>:
DELETE "idenifying"
INSERT --identifying--